(12) United States Patent
Shibayama et al.

(10) Patent No.: US 6,391,354 B1
(45) Date of Patent: May 21, 2002

(54) APPARATUS AND METHOD FOR SELECTING AND SEPARATING OUT SPROUTED KERNEL

(75) Inventors: Akira Shibayama; Tomoko Koshiro, both of Chiba (JP)

(73) Assignee: Anzai Universal Laboratory Co., Ltd., Chiba (JP)

( * ) Notice: Subject to any disclaimer, the term of this patent is extended or adjusted under 35 U.S.C. 154(b) by 0 days.

(21) Appl. No.: 09/994,757

(22) Filed: Nov. 28, 2001

(30) Foreign Application Priority Data

Aug. 23, 2001 (JP) ........................ 2001-252344

(51) Int. Cl.[7] ................. G01N 21/00; G01N 33/00
(52) U.S. Cl. ............... 426/231; 250/339.07; 250/458.1; 356/317; 426/240; 426/481
(58) Field of Search ................. 426/231, 240, 426/481; 250/339.07, 458.1; 356/317

(56) References Cited

U.S. PATENT DOCUMENTS 4,421,772 A * 12/1983 Munck et al. ............... 426/231
4,963,743 A * 10/1990 Satake et al. .......... 250/339.07

* cited by examiner

Primary Examiner—George C. Yeung
(74) Attorney, Agent, or Firm—Wenderoth, Lind & Ponack, L.L.P.

(57) ABSTRACT

An apparatus of the present invention for selecting and separating out sprouted kernel comprises: a light source for emitting light in a predetermined wavelength region to an object kernel; an image-capturing device for capturing an image of the object kernel which is formed by a part of the emitted light, which part is transmitted through the object kernel, and generating a signal corresponding to the captured image of the object kernel; a comparator for comparing the signal corresponding to the captured image with a predetermined reference signal, to thereby determine whether or not the object kernel is sprouted, and generating a signal indicative of detection of sprouting when the object kernel is sprouted; and a separating device for separating out the object kernel when the object kernel is sprouted, in response to the signal generated by the comparator. Below the object kernel, there is provided a background member having a brightness close to that of the object kernel. The light source is provided between the object kernel and the background member. Above the object kernel there is provided a slit-forming member.

8 Claims, 4 Drawing Sheets

GOOD-QUALITY GRAIN

POOR-QUALITY GRAIN

GOOD-QUALITY GRAIN

POOR-QUALITY GRAIN

APPARATUS AND METHOD FOR SELECTING AND SEPARATING OUT SPROUTED KERNEL

BACKGROUND OF THE INVENTION

The present invention relates to an apparatus and a method for selecting and separating out sprouted kernel, especially sprouted wheat kernel.

When kernel, such as wheat kernel, is subject to unseasonable weather during ripening stage or during harvesting stage, the kernel has a tendency to sprout. Sprouting of wheat kernel is especially problematic, because it leads to a reduction in starch viscosity (amylograph value) and a consequent lowering in quality of the kernel. Thus, it is necessary to separate out sprouted kernel following harvesting.

Thus far, no effective method for selecting and separating out sprouted kernel has been proposed; and only a method utilizing a specific gravity for selecting and separating out kernel which is severely sprouted has been employed.

This method exploits the fact that severely sprouted kernel has a far lower specific gravity as compared to non-sprouted kernel. However, while this method enables severely sprouted kernel to be separated from normal kernel, it does not enable kernel which is only slightly sprouted and yet of poor quality to be separated out. Use of this method utilizing a specific gravity is also subject to a drawback that variations in size and weight between individual non-sprouted kernels naturally occur, thereby making it difficult to set accurate parameters for identifying those kernels which are of good quality and those which are not. As a consequence, yields are lowered.

Therefore, an object of the present invention is to provide an apparatus and a method which enable effective selection and separation of sprouted kernel, including kernel which is only slightly sprouted.

One method that has been attempted in overcoming the problems of the above-mentioned method involves the use of reflective light, whereby a kernel surface is observed. However, this reflective-type method is not effective in differentiating poor-quality kernel (sprouted kernel) from good-quality kernel. This is due to the small size of kernel sprouts, unevenness of kernel surfaces and an absence of any clear difference in color between the surface of good-quality kernel and the surface of poor-quality kernel (see the illustration of FIG. 1).

Thus, the present inventors have attempted to detect sprouted kernel by transmitting light through the kernel. FIG. 2 is an illustration showing images of good-quality kernel and poor-quality kernel, which images are produced by the use of transmitted light. As is clear from FIG. 2, the present inventors have found a remarkable fact that when light is transmitted through kernel, good-quality kernel and poor-quality kernel produce distinctly different images. Namely, good-quality kernel produces a light image, while that of poor-quality kernel (sprouted kernel) includes a dark portion at and around a sprout contained in the kernel. The present inventors have also found that, in contrast to the method using reflective light, in the method using transmitted light, a degraded portion of a sprouted kernel is pronounced. Further, it has been found that a degraded portion can be easily identified, regardless of any unevenness in the kernel surface, which has been an obstacle to accomplishing effective selection using the reflective-type method.

When cut in section, a portion of a sprouted kernel around a sprout is seen to have a whitish color. The present inventors have found that this whitish portion of the kernel blocks the transmission of light, whereby an image of this portion produced by transmitted light is dark. On the basis of these findings, the present invention has been made. The basic technical idea of the invention involves selecting and separating out sprouted kernel by transmitting light through object kernel and observing images of the kernel formed by the transmitted light.

SUMMARY OF THE INVENTION

The present invention provides a method for selecting and separating out sprouted kernel, comprising the steps of: emitting light in a predetermined wavelength region to an object kernel; capturing an image of the object kernel which has been formed by a part of the emitted light, which part has been transmitted through the object kernel, and generating a signal corresponding to the captured image of the object kernel; comparing the signal corresponding to the captured image with a predetermined reference signal, to thereby determine whether or not the object kernel is sprouted; and separating out the object kernel when it has been determined that the object kernel is sprouted.

The present invention also provides an apparatus for selecting and separating out sprouted kernel, comprising: a light source for emitting light in a predetermined wavelength region to an object kernel; an image-capturing device for capturing an image of the object kernel which is formed by a part of the emitted light, which part is transmitted through the object kernel, and generating a signal corresponding to the captured image of the object kernel; a comparator for comparing the signal corresponding to the captured image with a predetermined reference signal, to thereby determine whether or not the object kernel is sprouted, and generating a signal indicative of detection of sprouting when the object kernel is sprouted; and a separating device for separating out the object kernel when the object kernel is sprouted, in response to the signal generated by the comparator.

Further, in the method and apparatus of the present invention, in order to easily detect sprouted kernel, a background member having a brightness substantially equal to that of the object kernel may be provided at the rear of the object kernel. Further, in order to restrict a field of view in which the kernel is observed, a slit-forming member which forms a slit having a predetermined size may be provided between the object kernel and the image-capturing device. The wavelength of light emitted from the light source is appropriately selected according to spectral characteristics (light transmittance) of the object kernel, and it is preferred to select the wavelength region in which the kernel has a high light transmittance. When the object kernel is a wheat kernel, the wavelength region of the light emitted from the light source is preferably from 700 nm to 1,150 nm. The separating device preferably includes an air gun capable of blowing off the object kernel. However, the separating device is not limited to a device including the air gun, and various means which are known in the art can be employed.

DETAILED DESCRIPTION OF THE INVENTION

Figure 1:
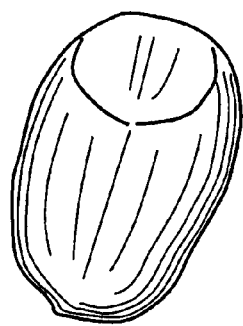
FIG. 1 is an illustration showing appearances of good-quality kernel (non-sprouted kernel) and poor-quality kernel (sprouted kernel).
Figure 1:
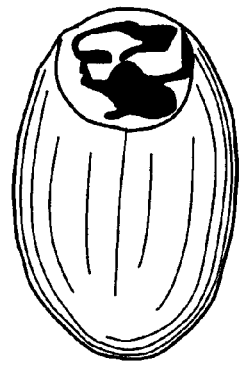
Figure 2:
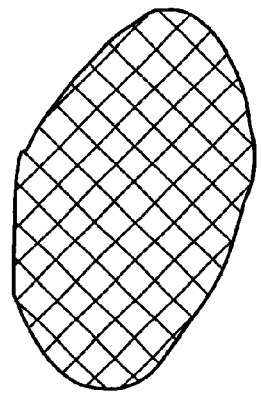
FIG. 2 is an illustration showing images of good-quality kernel (non-sprouted kernel) and poor-quality kernel (sprouted kernel), which images are produced by the use of transmitted light.
Figure 2:
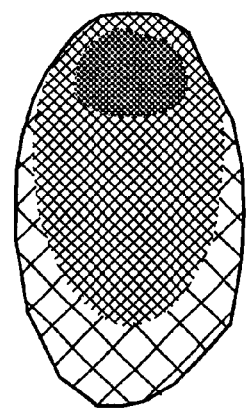
Figure 3:
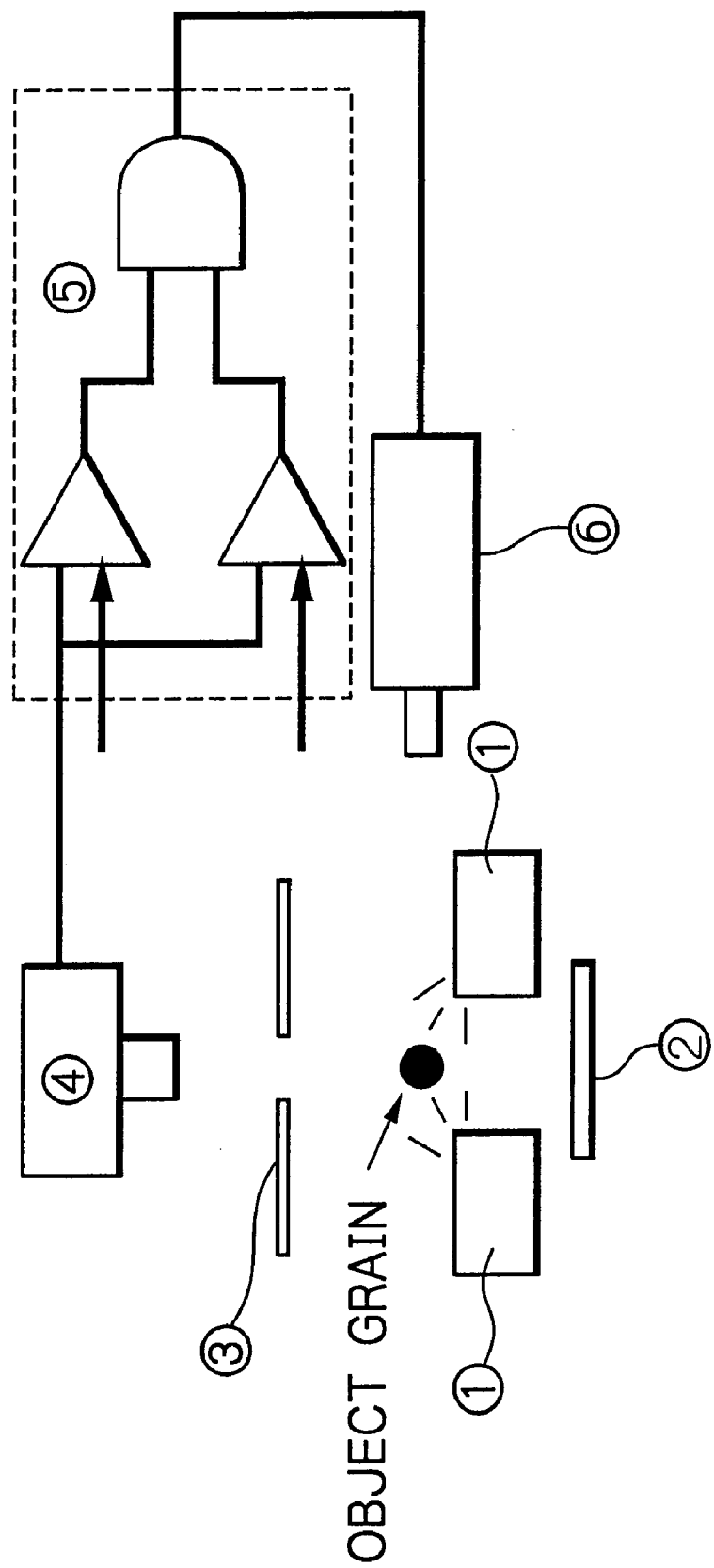
FIG. 3 is a general diagram of an apparatus of the present invention for selecting and separating out sprouted kernel.

Hereinbelow, an embodiment of the present invention is described in detail, with reference to the accompanying drawings. FIG. 3 is a general diagram of an apparatus of the present invention for selecting and separating out sprouted wheat kernel.

As shown in FIG. 3, a wheat kernel as an object kernel is irradiated with light, which is emitted from two light sources 1 provided obliquely below the kernel. The light sources 1 are adapted to emit light in a predetermined wavelength region. A background member 2 having a brightness close to that of the kernel is provided below the light sources 1. In order to restrict a field of view in which the kernel is observed, a slit-forming member 3 is provided above the kernel. A camera 4 is provided above the slit-forming member 3 at a position such that both the kernel and the background member 2 can be observed by the camera 4. An output side of the camera 4 is connected to a comparator 5. By this arrangement, an image of the kernel against the background member 2, which image is formed by light which has been transmitted through :the kernel, is captured by the camera 4. The image is fed in the form of an image signal from a line sensor of the camera 4 to the comparator 5. The comparator 5 compares the image signal with a reference signal which is preliminarily set for good-quality kernel, to thereby determine whether or not the kernel is sprouted, and outputs a signal corresponding to results of the determination. An output side of the comparator 5 is connected to an air gun device 6. The air gun device 6 generates a signal only when the comparator 5 determines that a kernel is sprouted. In response to this signal, air is blown from an air gun of the air gun device so as to blow off the kernel for separation. Thus, it is possible to conduct efficient selection and separation of sprouted kernel, including kernel which is only slightly sprouted.

Figure 4:
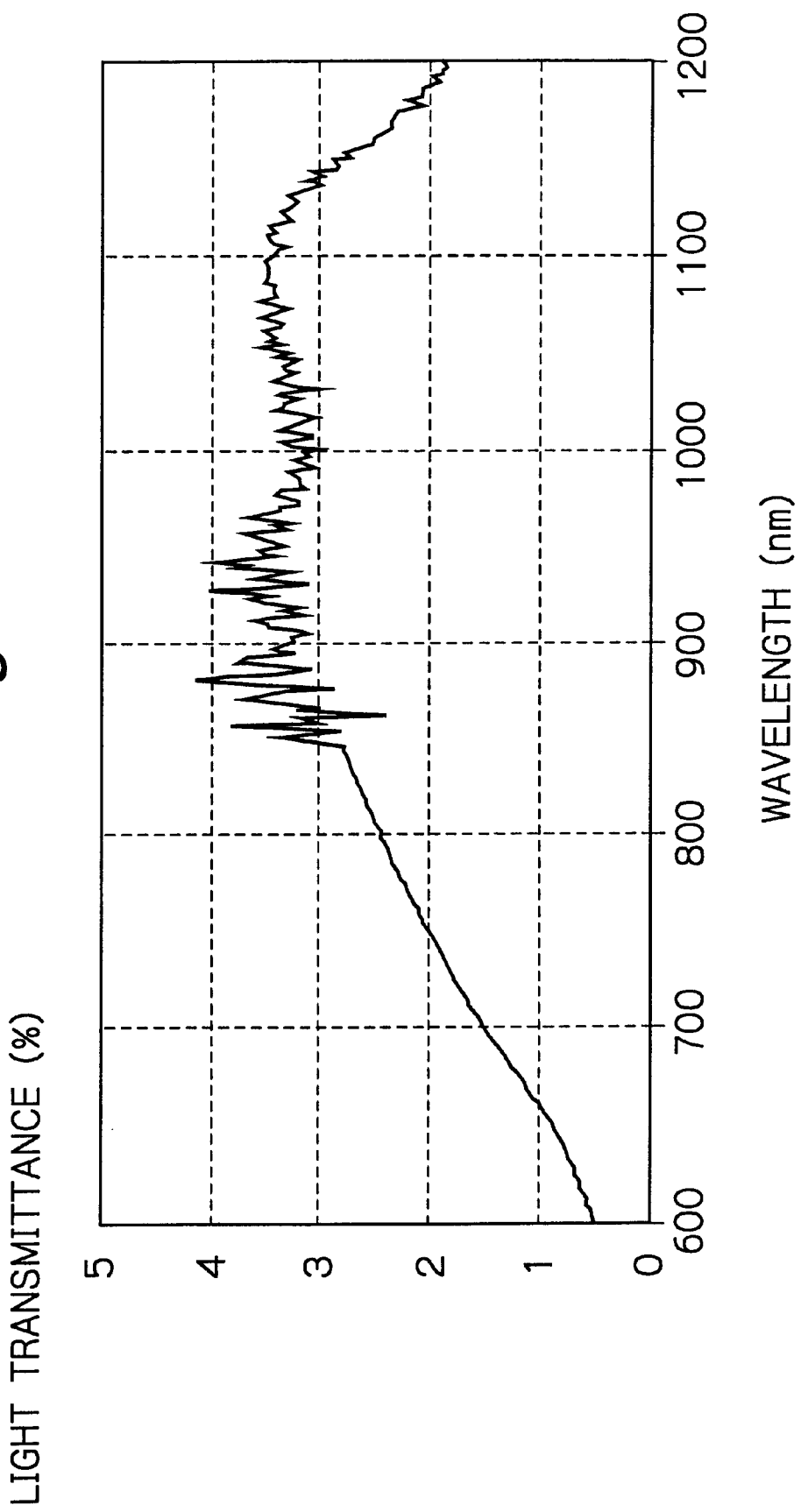
FIG. 4 is a graph showing spectral. characteristics of wheat kernel.

FIG. 4 is a graph showing spectral characteristics of wheat kernel. As is clear from FIG. 4, wheat kernel has a high light transmittance in a wavelength region of from about 700 nm to about 1,150 nm. Therefore, in the apparatus of FIG. 3 in which wheat kernel is observed, use is made of a light source which emits light in this wavelength region.

Figure 5:
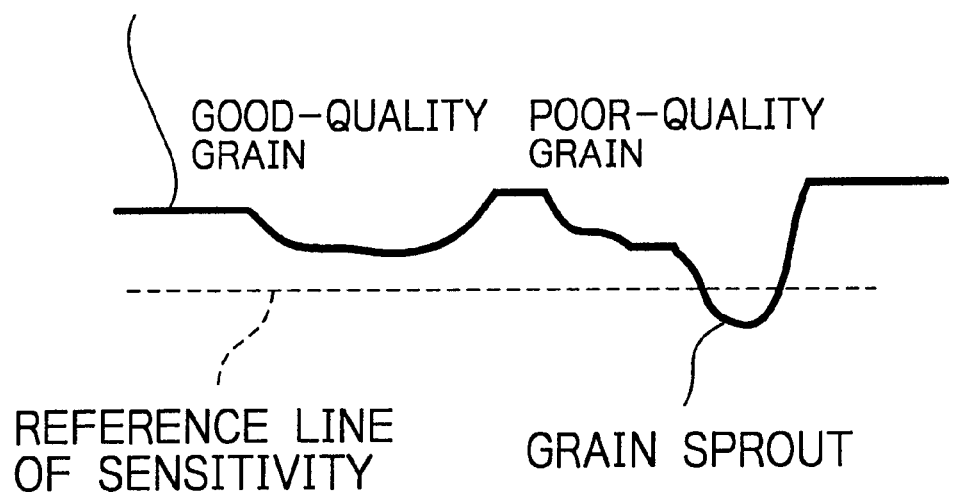
FIG. 5 is a diagram showing characteristics of a signal output from a camera, with respect to good-quality kernel (non-sprouted kernel) and poor-quality kernel (sprouted kernel).

Next, explanation is made with regard to an electric signal dealt with by the comparator 5. The light transmitted through an object kernel is converted into an electric signal by the camera 4. FIG. 5 is a diagram showing general characteristics of the electric signal. As is clear from FIG. 5, there is a large difference between the signal level of good-quality kernel and the signal level of poor-quality kernel (sprouted kernel). Therefore, by setting a reference signal level of the comparator 5 to an appropriate value between the signal level of good-quality kernel and the signal level of poor-quality kernel, accurate detection of sprouted kernel can be conducted by the comparator 5 by comparing the reference signal level with a signal level produced when a kernel has passed below the camera. When poor-quality kernel passes, the comparator 5 outputs a signal to operate the air gun.

Thus, in the present invention, selection and separation of sprouted kernel, which is difficult to conduct accurately using the conventional reflective-type method, can be accurately conducted by using an apparatus having a relatively simple structure. Further, in the present invention, due to the use of transmitted light, sprouted kernel can be easily identified, regardless of any unevenness in the kernel surface, which has been an obstacle to accomplishing effective selection using the reflective-type method.

What is claimed is:

1. A method for selecting and separating out sprouted kernel, comprising the steps of:

emitting light in a predetermined wavelength region to an object kernel;

capturing an image of the object kernel which has been formed by a part of the emitted light, which part has been transmitted through the object kernel, and generating a signal corresponding to the captured image of the object kernel;

comparing the signal corresponding to the captured image with a predetermined reference signal, to thereby determine whether or not the object kernel is sprouted; and separating out the object kernel when it has been determined that the object kernel is sprouted.

2. The method according to claim 1, wherein the object kernel is a wheat kernel and the wavelength region of the light emitted to the object kernel is from 700 nm to 1,150 nm.

3. The method according to claim 1, further comprising the step of providing, at the rear of the object kernel, a background member having a brightness substantially equal to a brightness of the object kernel.

4. An apparatus for selecting and separating out sprouted kernel, comprising:

a light source for emitting light in a predetermined wavelength region to an object kernel;

an image-capturing device for capturing an image of the object kernel which is formed by a part of the emitted light, which part is transmitted through the object kernel, and generating a signal corresponding to the captured image of the object kernel;

a comparator for comparing the signal corresponding to the captured image with a predetermined reference signal, to thereby determine whether or not the object kernel is sprouted, and generating a signal indicative of detection of sprouting when the object kernel is sprouted; and a separating device for separating out the object kernel when the object kernel is sprouted, in response to the signal generated by the comparator.

5. The apparatus according to claim 4, wherein the object kernel is a wheat kernel and the wavelength region of the light emitted to the object kernel is from 700 nm to 1,150 nm.

6. The apparatus according to claim 4, further comprising a background member provided at the rear of the object kernel, the background member having a brightness substantially equal to a brightness of the object kernel.

7. The apparatus according to claim 4, further comprising a slit-forming member provided between the object kernel and the image-capturing device, the slit-forming member forming a slit having a predetermined size.

8. The apparatus according to claim 4, wherein the separating device includes an air gun for blowing off the object kernel.

* * * * *